US012806697B2

United States Patent
(12) Arai et al.

(10) Patent No.: US 12,806,697 B2
(45) Date of Patent: Nov. 24, 2026

(54) DRILL

(71) Applicant: BIC TOOL CO., LTD., Tottori (JP)

(72) Inventors: Koichi Arai, Tottori (JP); Giichi Arai, Tottori (JP); Katsuyo Kimura, Tottori (JP); Satoshi Teshima, Tottori (JP)

(73) Assignee: BIC TOOL CO., LTD., Tottori (JP)

(*) Notice: Subject to any disclaimer, the term of this patent is extended or adjusted under 35 U.S.C. 154(b) by 24 days.

(21) Appl. No.: 18/569,556

(22) PCT Filed: Jul. 27, 2022

(86) PCT No.: PCT/JP2022/029018
§ 371 (c)(1),
(2) Date: Dec. 12, 2023

(87) PCT Pub. No.: WO2023/176003
PCT Pub. Date: Sep. 21, 2023

(65) Prior Publication Data
US 2024/0217007 A1 Jul. 4, 2024

(30) Foreign Application Priority Data
Mar. 15, 2022 (JP) ................................ 2022-040439

(51) Int. Cl.
*B23B 51/02* (2006.01)
*A61B 17/16* (2006.01)

(52) U.S. Cl.
CPC ............. *B23B 51/02* (2013.01); *A61B 17/16* (2013.01); *B23B 2251/082* (2013.01);
(Continued)

(58) Field of Classification Search
CPC .............. B23B 51/02; B23B 2251/443; B23B 2251/14; B23B 2251/40;
(Continued)

(56) References Cited

U.S. PATENT DOCUMENTS 1,859,202 A * 5/1932 Emmons ............... E21B 10/445 175/395
3,237,488 A * 3/1966 Parone .................... B23B 51/02 408/230
(Continued)

FOREIGN PATENT DOCUMENTS

JP H10-315024 A 12/1998
JP 2005305610 A 11/2005
(Continued)

*Primary Examiner* — Jermie E Cozart
(74) *Attorney, Agent, or Firm* — KELLY & KELLEY, PLLC

(57) ABSTRACT

The problem to be solved is to provide a drill that is difficult to break and has a good cutting ability. The drill according to the present invention comprises: a first and a second cutting edge formed symmetrically with respect to a rotation axis; a first and a second relief surface formed symmetrically with respect to the rotation axis on back surfaces of the first and the second cutting edge, respectively; one chip-discharging groove formed from one of the first and the second cutting edge toward an outer peripheral side; and one or more arc-shaped grooves formed from another of the first and the second cutting edge toward the outer peripheral side.

1 Claim, 7 Drawing Sheets

(52) U.S. Cl.
CPC ... *B23B 2251/0825* (2022.01); *B23B 2251/14* (2013.01); *B23B 2251/18* (2013.01); *B23B 2251/40* (2013.01); *B23B 2251/443* (2013.01)

(58) Field of Classification Search
CPC ...... B23B 2251/0825; B23B 2251/082; B23B 2251/18; A61B 17/16
See application file for complete search history.

(56) References Cited

U.S. PATENT DOCUMENTS

| | | | | |
|---|---|---|---|---|
| 4,688,972 | A * | 8/1987 | Kubota | B23B 51/02 408/230 |
| 6,315,504 | B1 * | 11/2001 | Sekiguchi | B23B 51/02 408/229 |
| 2006/0269372 | A1 * | 11/2006 | Goshima | B23B 51/02 408/230 |
| 2008/0019787 | A1 * | 1/2008 | Sampath | B23B 51/02 408/230 |
| 2008/0080940 | A1 * | 4/2008 | Sorensen | B23B 51/009 408/223 |
| 2009/0016832 | A1 * | 1/2009 | Onose | B23B 51/06 408/230 |
| 2010/0054884 | A1 * | 3/2010 | Masuda | B23B 51/02 408/230 |
| 2012/0301239 | A1 * | 11/2012 | Prom | B23B 51/02 408/226 |
| 2013/0017029 | A1 * | 1/2013 | Sun | B23B 51/02 408/227 |
| 2013/0142583 | A1 * | 6/2013 | Arai | B24B 3/32 408/229 |
| 2016/0214184 | A1 * | 7/2016 | Krenzer | B23B 51/02 |
| 2018/0043441 | A1 * | 2/2018 | Fujiwara | B23B 51/02 |
| 2019/0308254 | A1 * | 10/2019 | Arai | B23B 51/02 |
| 2019/0314039 | A1 * | 10/2019 | Guter | A61B 17/1615 |
| 2020/0030893 | A1 * | 1/2020 | Krenzer | B23B 51/02 |
| 2020/0114434 | A1 * | 4/2020 | Ogawa | B23B 51/009 |
| 2020/0282472 | A1 * | 9/2020 | Yamamoto | B23B 51/02 |
| 2021/0260670 | A1 | 8/2021 | Naito et al. | |
| 2022/0241873 | A1 * | 8/2022 | Arai | B23B 51/02 |

FOREIGN PATENT DOCUMENTS

| | | | |
|---|---|---|---|
| JP | 2006088267 | A | 4/2006 |
| JP | 2012056055 | A | 6/2012 |
| JP | 2012192524 | A | 10/2012 |
| JP | 2018108223 | A | 7/2018 |
| JP | 2018108224 | A | 7/2018 |
| JP | 2018167341 | A | 11/2018 |
| JP | 2021038651 | A1 | 4/2021 |

* cited by examiner

PRIOR ART

DRILL

FIELD OF THE INVENTION

The present invention relates to a drill. More specifically, the present invention relates to a drill with superior rotational torque resistance and cutting ability which is used not only for drilling holes in a workpiece such as a metal plate with a hand drill, a drill press, or the like without breakage, but also used for drilling holes directly in a surgical area during a medical surgery, especially in an orthopedic surgery.

BACKGROUND OF THE INVENTION

A conventional two-edge drill with two cutting edges, having two chip-discharging grooves formed point-symmetrically with respect to the center of rotation to helically extend toward the rearward end of the drill, is commonly used at the forward end of a drill body that rotates about the axis of the drill.

Since drills used for general industrial use, such as hand drills and drill presses, utilize force exerted by the operator's arms to drill holes, it is difficult to drill holes when the cutting resistance is high.

However, manufacturers of drills have spent little time on research for decreasing cutting resistance, since they thought that strength and stiffness should be ensured first for these drills themselves, and in practice, operators who bought these drills would grind the drills to use them as they desired.

The present applicant has proposed a drill for general industrial use that is preferably used for peeling spot welding of a vehicle body made of high-hardness steel plate (Refer to Japanese Unexamined Patent Application Publication No. 2006-088267).

This drill has two cutting edges that are symmetrical around the rotation axis and are thinned at the forward end so that the chisel width is from 0.05 mm to 0.3 mm and the web is subject to thinning at an angle from 1° to 4° toward the straight line that connects between the tips of the two cutting edges when viewed from the side of the drill forward end.

Further, the applicant has proposed a drill for general industrial use that can significantly decrease cutting resistance and can facilitate the operation of drilling holes with a hand drill, a drill press, or the like using the force exerted by the operator (Refer to Japanese Unexamined Patent Application Publication No. 2012-192514)

This drill has two cutting edges that are symmetrical around the rotation axis and are thinned at the forward end so that the rake angle $\theta 1$ formed by each main cutting edge and the rake angle $\theta 2$ formed by each thinned cutting edge satisfy $\theta 1 > \theta 2 > 0°$, except directly below the chisel.

As such, in the conventional two-edge drill, since chip-discharging grooves are provided from the forward end to the outer periphery, the thinned center portion may lead to breakage during the operation, and thus the center portion is formed thicker to some extent to ensure the strength of the center portion, and the center portion of the forward end is made thin by the thinning process.

Further, a drill that is thinned at the forward end, and has second margin portions arranged to comprise outer periphery edges of the intersection ridge line between the forward end relief surfaces and the thinned portions when viewed from the side of the forward end in the axial direction and further arranged to be separated by a predetermined distance from the heels of the cutting edge portions to the forward side in the drill rotation direction is also well known (Refer to Japanese Unexamined Patent Application Publication No. 2005-305610).

The applicant has also proposed a drill having a shape that improves the cutting ability of a conventional drill and a drill for medical use to be used for orthopedic or other medical surgeries (Refer to Japanese Unexamined Patent Application Publication No. 2018-108223).

Furthermore, the applicant has also proposed a drill, a so-called Kirschner wire, as a drill for medical use that has no chip-discharging groove provided but an inclination provided from the round bar shape to the forward end and a thinly formed, drill-shaped forward end (Refer to Japanese Unexamined Patent Application Publication No. 2018-108224).

SUMMARY OF THE INVENTION

Problems to be Solved by the Invention

Forming a chip-discharging groove shallowly results in extremely poor cutting ability, and providing two chip-discharging grooves on the outer periphery of a drill results in reduced strength; the above problems are contradictory to each other and have not been solved yet.

Especially, in the case of a small-diameter drill such as a guide pin, a conventional medical drill has a shape of a small diameter of approximately 2 mm and a long overall length, and furthermore rarely drills towards a surgical area vertically like an industrial drill, but in many cases drills inclining toward the horizontal direction.

Since the drilling is to be performed at an incline in such a way, the portion with a chip-discharging groove may break more easily in terms of strength; moreover, similar to the strength, it is also inferior in stiffness, and thus the forward end may slip easily when drilling at an inclined portion, and it may not be able to drill accurately into the target point. To solve these problems, the aforementioned Japanese Unexamined Patent Application Publication No. 2018-108224 tries to overcome the problems with a so-called Kirschner steel wire that has a thinly formed, drill-shaped forward end, but since this shape is merely a rod with a sharp forward end and has inferior cutting ability, there are concerns such as inducing heat during bone drilling, which may lead to osteonecrosis.

In the case of the drill described in the aforementioned Japanese Unexamined Patent Application Publication No. 2018-108223, since thinning process is applied to a chisel portion of a forward end from two sides of a chip-discharging groove to the center of a drill in order to reduce cutting resistance, the chip-discharging groove cannot be formed up to near the center portion of the drill.

Japanese Unexamined Patent Application Publication No. 2018-108223 and Japanese Unexamined Patent Application Publication No. 2018-108224 both disclose an embodiment that is formed by an arc-shaped groove. The arc shape of this embodiment does not solve the problems of chip discharging and adhesion between the already drilled hole and the outer periphery of the drill.

The present invention is to solve the problems in prior art described above and provide a drill that is difficult to break and has a good cutting ability.

Means for Solving the Problems

In order to achieve the aforementioned objective, the invention according to a first aspect relates to a drill comprising:

- a first and a second cutting edge formed symmetrically with respect to a rotation axis;
- a first and a second relief surface formed symmetrically with respect to the rotation axis on back surfaces of the first and the second cutting edge, respectively;
- one chip-discharging groove formed from one of the first and the second cutting edge toward an outer peripheral side; and
- one or more arc-shaped grooves formed from another of the first and the second cutting edge toward the outer peripheral side.

The invention according to a second aspect relates to the drill according to the first aspect, wherein only one of the arc-shaped grooves is formed, a third relief surface is formed between the one arc-shaped groove and the first relief surface, the one arc-shaped groove and the second relief surface are adjacent to each other, and the one arc-shaped groove and the first relief surface are partially adjacent to each other.

The invention according to a third aspect relates to the drill according to the first aspect, wherein two or more of the arc-shaped grooves are formed to be adjacent to each other, one of the two or more arc-shaped grooves and the first relief surface are partially adjacent to each other, and another one of the two or more arc-shaped grooves and the second relief surface are adjacent to each other.

The invention according to a fourth aspect relates to the drill according to any one of the first to the third aspects, wherein the first and the second cutting edge are provided with a first and a second back groove from the rearward ends of the outer peripheries of the first and the second cutting edge to the first and the second relief surface, respectively, and also provided with a first and a second margin portion of the first and the second cutting edge, respectively.

Effects of the Invention

According to the first aspect of the present invention, a drill is equipped with a first and a second cutting edge formed symmetrically with respect to a rotation axis; a first and a second relief surface formed symmetrically with respect to the rotation axis on back surfaces of the first and the second cutting edge, respectively; one chip-discharging groove formed from one of the first and the second cutting edge toward an outer peripheral side; and one or more arc-shaped grooves formed from another of the first and the second cutting edge toward the outer peripheral side; and ensures both cutting ability and strength, and thus breakage of the drill can be prevented.

Without a thinning process applied, the chip-discharging groove can be formed up to near the center portion of the drill, and thus the chip-discharging groove itself can exhibit the same effect (i.e., good cutting ability) as if a thinning process is applied.

Since the drill comprises the first and the second relief surface formed symmetrically with respect to the rotation axis, the occurrence of troubles such as the center portion being out of control at the start of drilling is suppressed.

According to the second aspect of the present invention, a drill is equipped with a configuration wherein only one of the arc-shaped grooves is formed, a third relief surface is formed between the one arc-shaped groove and the first relief surface, the one arc-shaped groove and the second relief surface are adjacent to each other, and the one arc-shaped groove and the first relief surface are partially adjacent to each other; and together with the configuration of that in the first aspect, the back surfaces of the first and the second cutting edge form the first and the second relief surface similarly to a conventional two-edged drill, and the third relief surface is provided at the side of the rearward heel of the first relief surface which has no chip-discharging groove, thereby interference with the relief surface during drilling can be avoided.

According to the third aspect of the present invention, a drill is equipped with a configuration wherein two or more of the arc-shaped grooves are formed to be adjacent to each other, two or more of the two or more arc-shaped grooves and the first relief surface are partially adjacent to each other, and another of the two or more arc-shaped grooves and the second relief surface are adjacent to each other, and thus a small amount of chips generated by the second cutting edge may remain. Therefore, further grooves approximately parallel to the groove forming the second cutting edge are provided, thereby the interference with the relief surfaces during drilling and the problem of chips remaining can be avoided.

According to the fourth aspect of the present invention, a drill is equipped with a configuration wherein the first and the second cutting edge are provided with a first and a second back groove from the rearward ends of the outer peripheries of the first and the second cutting edge to the first and the second relief surface, respectively, and also provided with a first and a second margin portion of the first and the second cutting edge, respectively, and thus even if the diameter of the drill is increased, the drill will not be affected by frictional resistance of the outer peripheries.

DETAILED DESCRIPTION OF THE INVENTION

Embodiments of a drill of the present invention are explained below with reference to the accompanying drawings.

Figure 1:
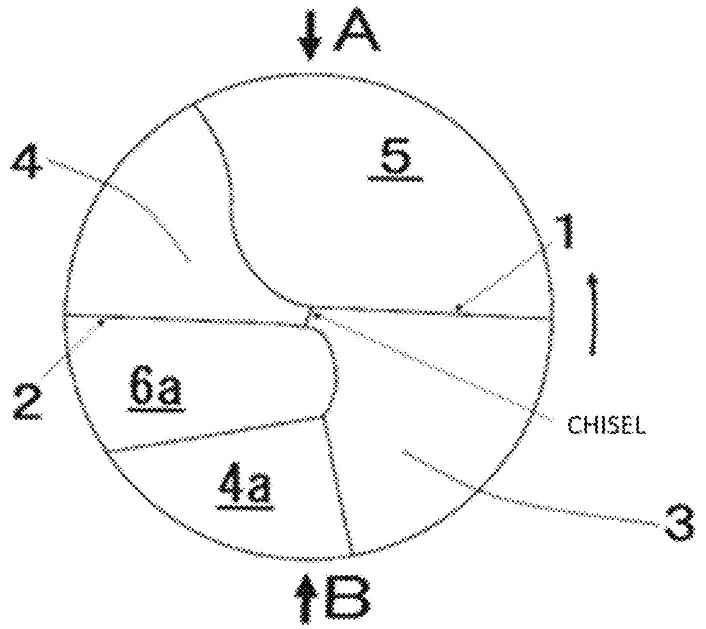
FIG. 1 is a front view showing the forward end of a drill according to an embodiment of the present invention.
Figure 2:
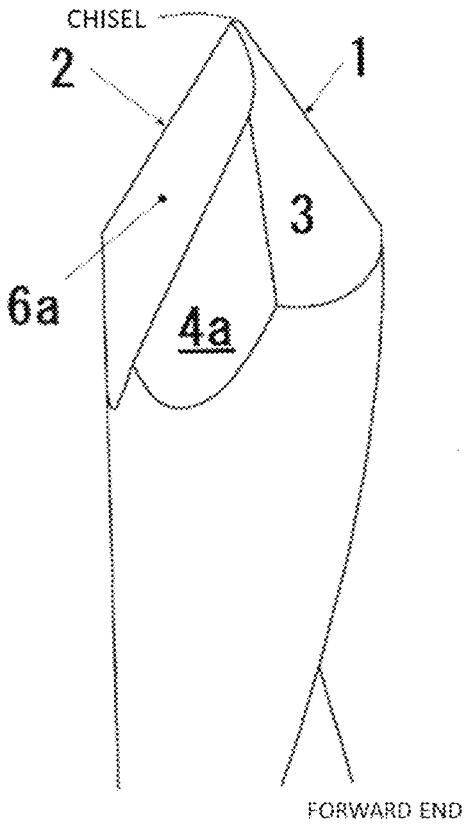
FIG. 2 is a bottom view of the forward end of the drill in FIG. 1 as viewed from the direction of arrow B.
Figure 3:
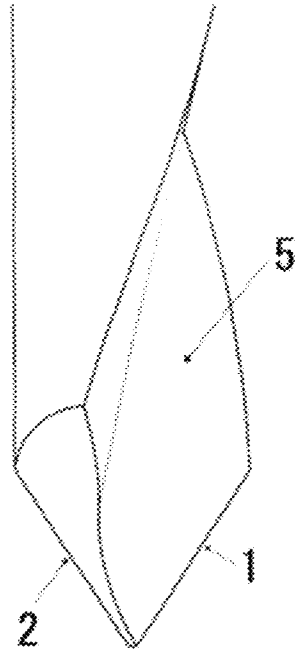
FIG. 3 is a top view of the forward end of the drill in FIG. 1 as viewed from the direction of arrow A.
Figure 4:
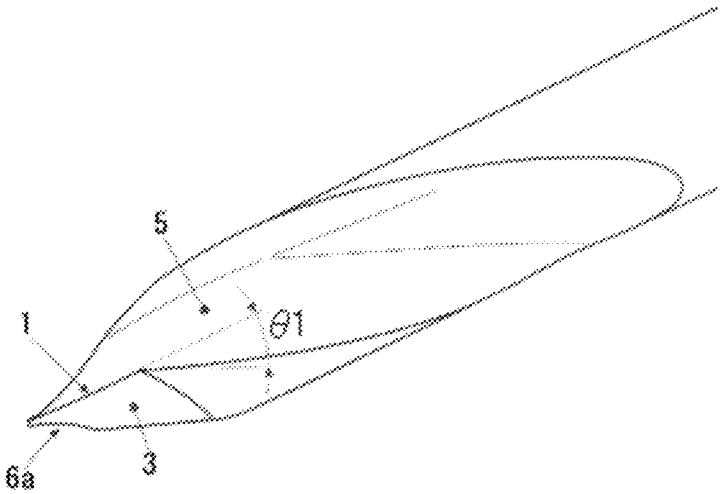
FIG. 4 is a perspective view showing the first cutting edge of the drill in FIG. 1.
Figure 5:
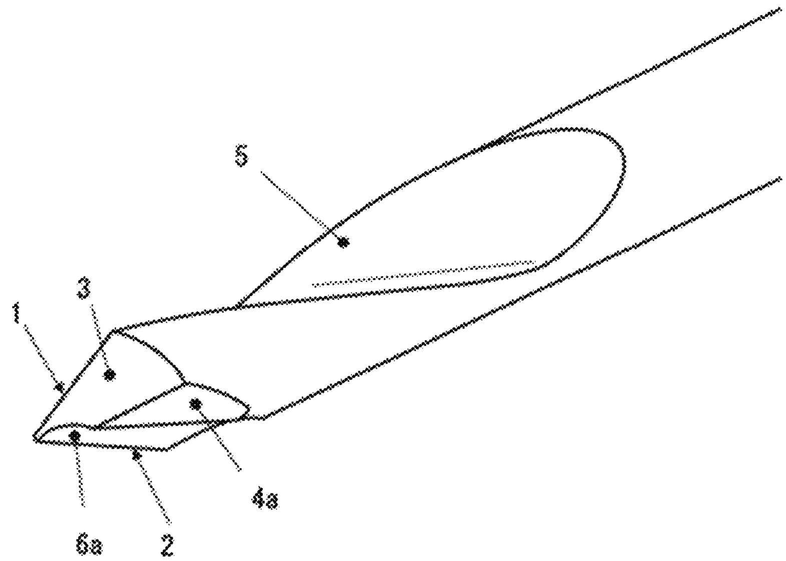
FIG. 5 is a perspective view of the drill in FIG. 4, rotated by about 45° about an axis.
Figure 6:
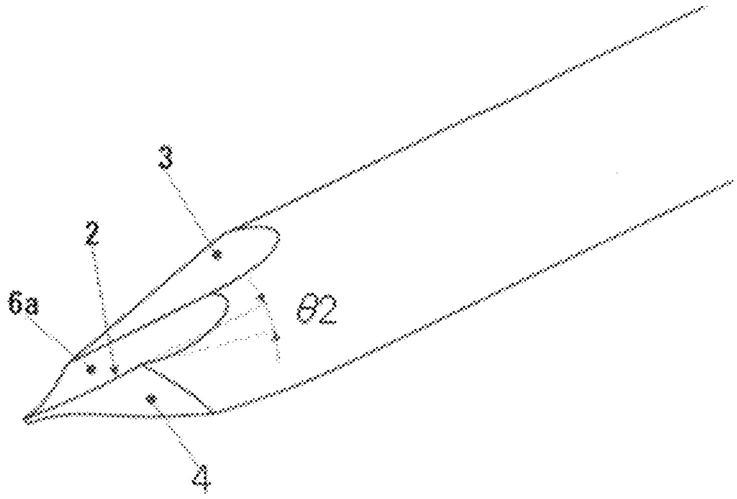
FIG. 6 is a perspective view of the drill in FIG. 4, rotated by about half a turn.
Figure 7:
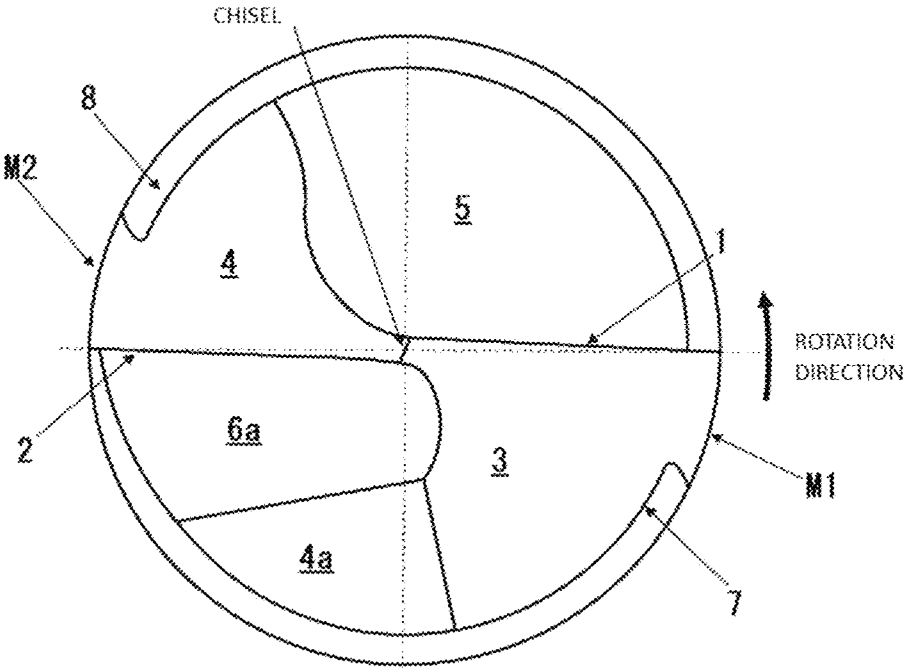
FIG. 7 is a front view showing the forward end of a drill according to another embodiment of the present invention.
Figure 8:
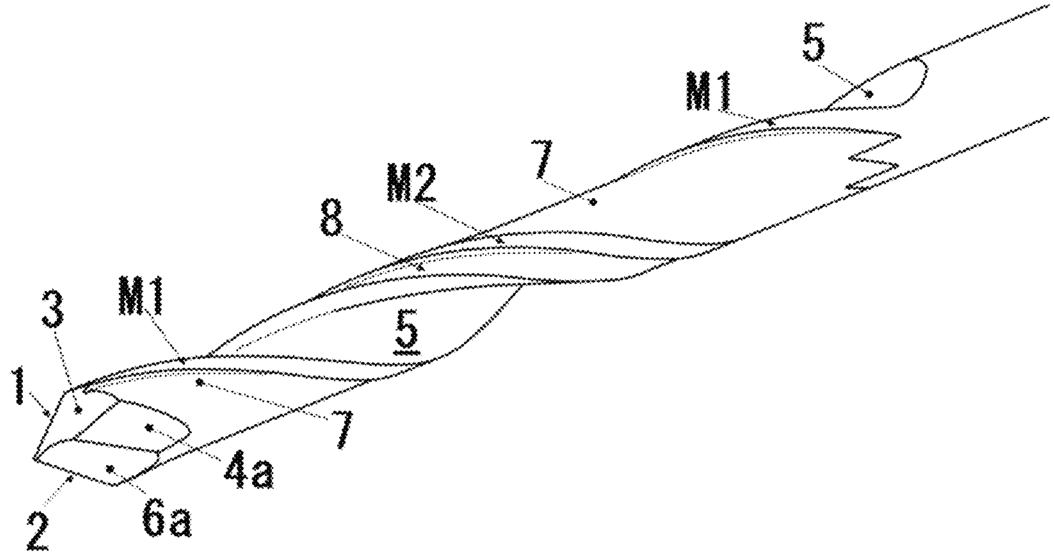
FIG. 8 is a perspective view of the drill in FIG. 7.
Figure 9:
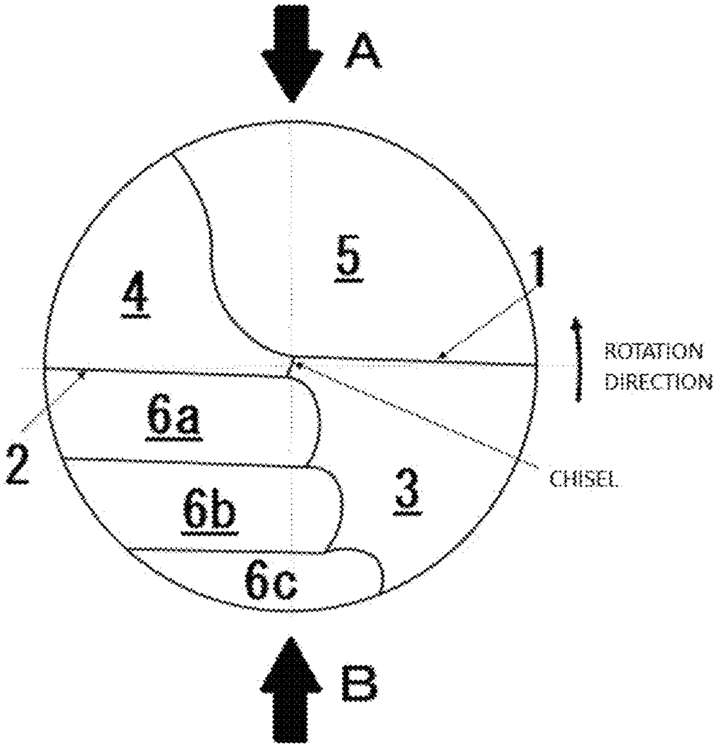
FIG. 9 is a front view showing the forward end of a drill according to yet another embodiment of the present invention.
Figure 10:
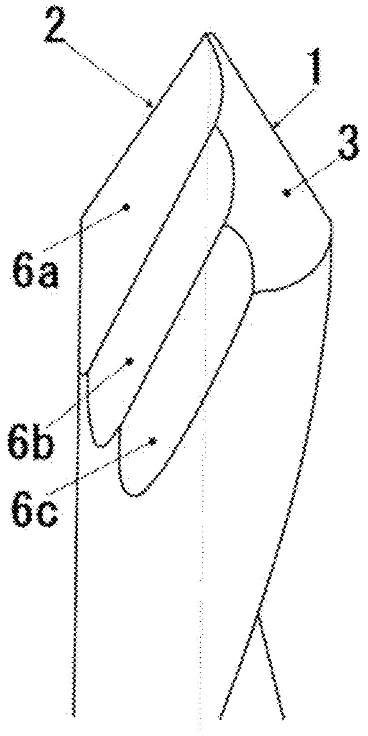
FIG. 10 is a bottom view of the forward end of the drill in FIG. 9 as viewed from the direction of arrow B.
Figure 11:
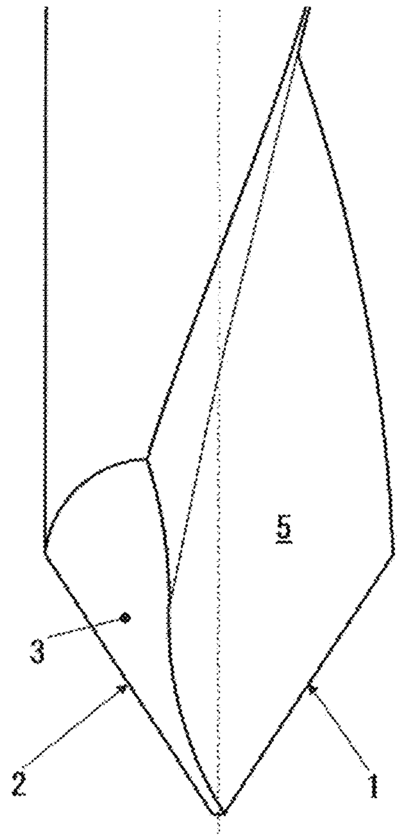
FIG. 11 is a top view of the forward end of the drill in FIG. 9 as viewed from the direction of arrow A.
Figure 12:
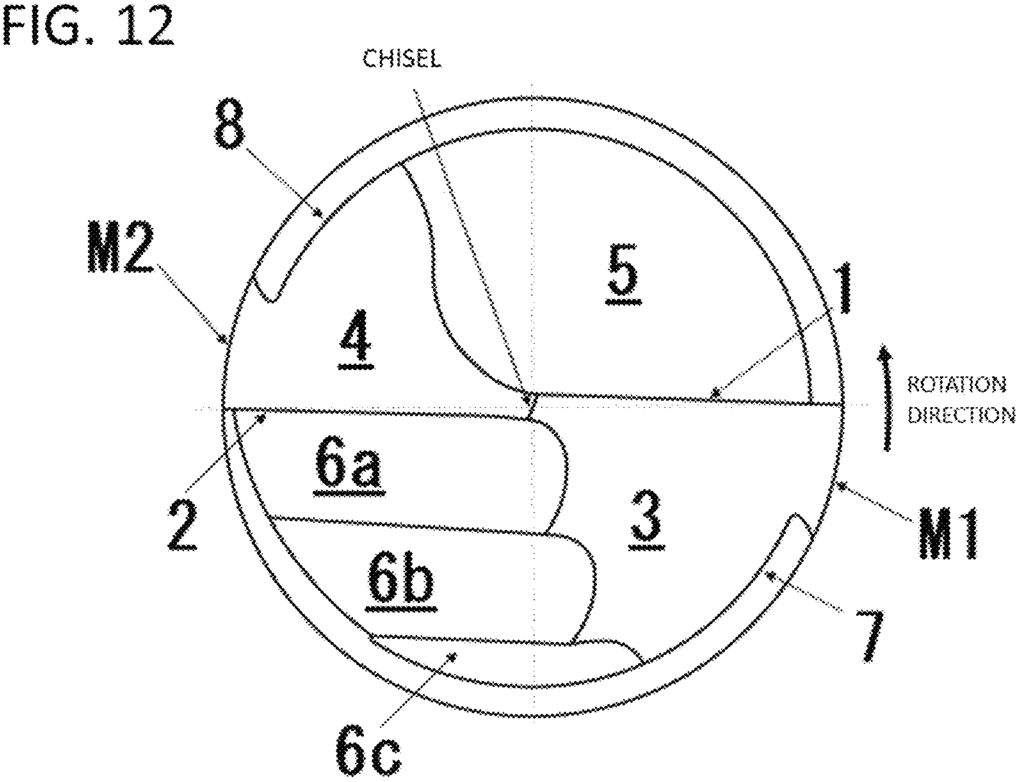
FIG. 12 is a front view showing the forward end of a drill according to yet another embodiment of the present invention.
Figure 13:
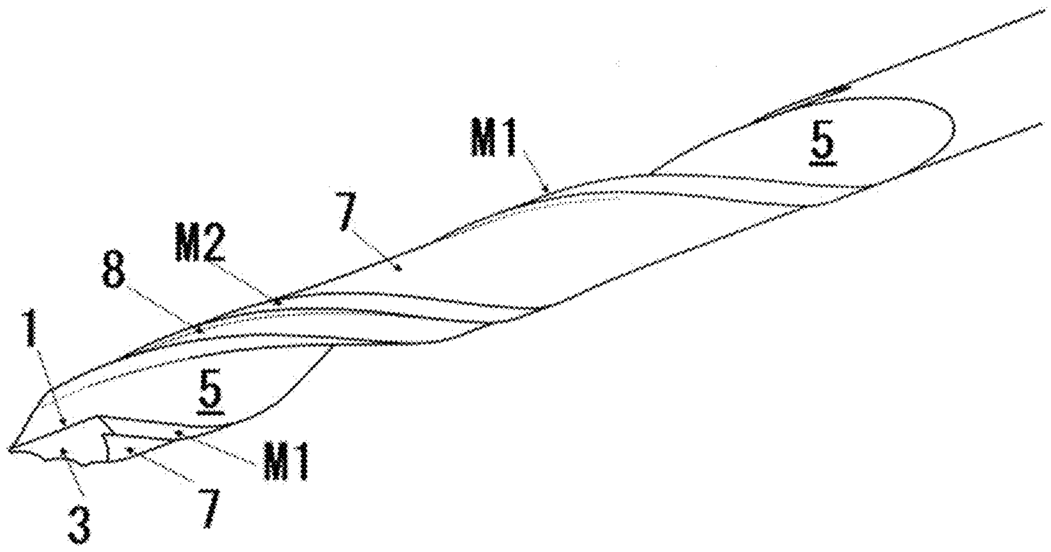
FIG. 13 is a perspective view of the drill in FIG. 12.
Figure 14:
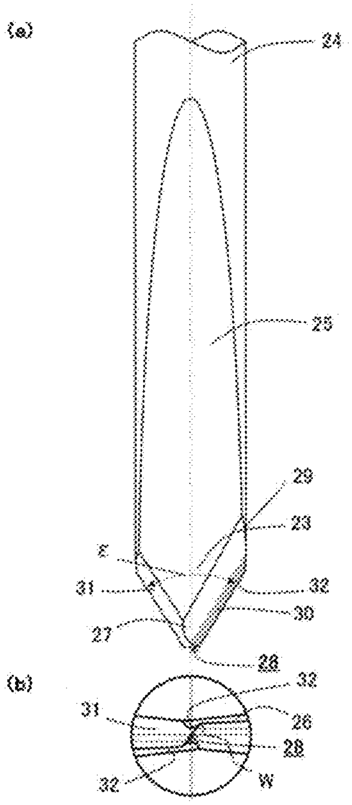
FIG. 14 is an explanatory drawing of a conventional drill.

FIG. 1 is a front view showing the forward end of a drill according to an embodiment of the present invention. FIG. 2 is a bottom view of the forward end of the drill in FIG. 1 as viewed from the direction of arrow B. FIG. 3 is a top view of the forward end of the drill in FIG. 1 as viewed from the direction of arrow A. FIG. 4 is a perspective view showing the first cutting edge of the drill in FIG. 1. FIG. 5 is a perspective view of the drill in FIG. 4, rotated by about 45° about an axis. FIG. 6 is a perspective view of the drill in FIG. 4, rotated by about half a turn. FIG. 7 is a front view showing the forward end of a drill according to another embodiment of the present invention. FIG. 8 is a perspective view of the drill in FIG. 7. FIG. 9 is a front view showing the forward end of a drill according to yet another embodiment of the present invention. FIG. 10 is a bottom view of the forward end of the drill in FIG. 9 as viewed from the direction of arrow B. FIG. 11 is a top view of the forward end of the drill in FIG. 9 as viewed from the direction of arrow A. FIG. 12 is a front view showing the forward end of a drill according to yet another embodiment of the present invention. FIG. 13 is a perspective view of the drill in FIG. 12.

Referring to FIGS. 1 to 4, the drill (D) according to the present embodiment comprises a first cutting edge (1) and a second cutting edge (2) formed symmetrically with respect to a rotation axis; a first relief surface (3) and a second relief surface (4) formed symmetrically with respect to the rotation axis on back surfaces of the first cutting edge (1) and the second cutting edge (2), respectively; one chip-discharging groove (5) formed from one of the first cutting edge (1) and the second cutting edge (2) (e.g., the first cutting edge (1)) toward an outer peripheral side; and one arc-shaped groove (6) formed from another of the first cutting edge (1) and the second cutting edge (2) (e.g., the second cutting edge (2)) toward the outer peripheral side.

Although only one arc-shaped groove (6) is illustrated in FIGS. 1 to 4, the number of arc-shaped grooves (6) is not limited to one, but may be two or three, for example.

The second cutting edge (2) is formed by the arc-shaped groove (6), and for this arc-shaped groove (6), the rake angle (θ2) of the second cutting edge (2) is set to be greater than 0° and within 5° (i.e., $0° < θ2 < 5°$).

A rake angle (θ1) of the first cutting edge (1) is formed by the helix angle of the chip-discharging groove (5), and since the rake angle (θ1) differs between the center portion and the outer periphery, the rake angle (θ1) will not be the same, but the rake angle (θ1) is always formed to have a positive rake angle (θ1) (i.e., $θ1 > 0°$). The reason why the rake angle (θ1) is set to be positive in such manner is that having a negative rake angle (θ1) will increase the cutting resistance of the drill (D) and result in poor cutting ability.

The arc forming the arc-shaped groove (6) which is the rake portion of the second cutting edge (2), may be formed with a single radius, two or more different radii, or a part of an oval shape as the shape of the groove.

Since the drill (D) according to the present embodiment comprises the configuration described above, breakage of the drill (D) can be prevented. Further, since the drill (D) according to the present embodiment is not thinned, and the chip-discharging groove (5) can be formed up to near the center portion of the drill (D), the chip-discharging groove (5) itself can exhibit the same effect (i.e., good cutting ability) as if a thinning process is applied.

Since the drill (D) according to the present embodiment, as mentioned above, comprises a first relief surface (3) and a second relief surface (4) formed symmetrically with respect to the rotation axis, the occurrence of troubles such as the center portion being out of control at the start of drilling is suppressed.

Variation of Embodiment 1

Referring to FIG. 1, the drill (D) according to a variation of the aforementioned Embodiment 1 is equipped with a configuration wherein only one of the arc-shaped grooves (6) is formed, a third relief surface (4*a*) is formed between the only one arc-shaped groove (6*a*) and the first relief surface (3), the only one arc-shaped groove (6*a*) and the second relief surface (4) are adjacent to each other, and the only one arc-shaped groove (6*a*) and the first relief surface (3) are partially adjacent to each other.

Since the drill (D) according to the variation is equipped with such a configuration, together with the configuration of the first aspect of the drill according to the aforementioned Embodiment 1, the back surfaces of the first cutting edge (1) and the second cutting edge (2) form a first relief surface (3) and a second relief surface (4) similarly to a conventional two-edge drill, and a third relief surface (4*a*) is provided at the side of the rearward heel of the first relief surface (3) which has no chip-discharging groove to avoid interference with the relief surface during drilling.

Referring to FIGS. 7-8, the drill (D) according to a further variation of the aforementioned Embodiment 1 is equipped with a configuration wherein the first cutting edge (1) and the second cutting edge (2) are provided with a first back groove (7) and a second back groove (8) from the rearward ends of the outer peripheries of the first cutting edge (1) and the second cutting edge (2) to the first relief surface (3) and the second relief surface (4), respectively, and also provided with a first margin portion (M1) and a second margin portion (M2) of the first cutting edge (1) and the second cutting edge (2), respectively.

Therefore, the drill (D) according to the present variation would not be affected by the frictional resistance of the outer periphery even if the diameter of the drill (D) is increased.

In more detail, the first back groove (7) and the second back groove (8) as well as the first margin portion (M1) and the second margin portion (M2) can be formed on the outer peripheries as appropriate depending on the drilling depth, and the portions with the first back groove (7) and the second backgroove (8) are thinner than the first margin portion (M1) and the second margin portion (M2), thus only the first margin portion (M1) and the second margin portion (M2) will be in contact with the wall surface of the drilled hole, thereby reducing friction during drilling.

Embodiment 2

Referring to FIGS. 9 to 11, the drill (D) according to the present embodiment is equipped with a configuration wherein three of the arc-shaped groove (6*a*) of the drill (D) according to Embodiment 1 are formed to be adjacent to each other, the three arc-shaped grooves (6*a*, 6*b*, 6*c*) and the first relief surface (3) are partially adjacent to each other, and one of the three arc-shaped grooves (6*a*, 6*b*, 6*c*) (i.e., arc-shaped groove (6*a*)) is adjacent, and thus a small amount of chips generated by the second cutting edge (2) may remain. Therefore, further grooves (i.e., arc-shaped grooves (6*b*, 6*c*)) approximately parallel to the groove (i.e., arc-shaped groove (6*a*)) forming the second cutting edge (2) are provided, thereby the interference with the relief surface during drilling and the problem of chips remaining can be avoided.

The number of grooves (i.e., arc-shaped grooves) may be one or more, but since providing too many grooves will affect the aforementioned problem of strength, it is desirable to provide about one or two or more grooves other than the groove (i.e., arc-shaped groove (6*a*)) forming the second cutting edge (2). Further, the depth of the grooves (i.e., arc-shaped grooves (6*b*, 6*c*)) is set equal to or shallower than the arc-shaped groove (6*a*).

The number of grooves may be determined depending on the width, and depth or the like of the grooves, and the depth of the grooves may also be set in consideration of strength or other factors. Further, by forming an approximately straight ridgeline at the point to which each of the three arc-shaped grooves (6*a*, 6*b*, 6*c*) is adjacent, gaps are generated from the cylindrical portion, thereby solving the problem of chips, and the number of grooves can be determined depending on the depth of the drilling portion, thereby solving the problem of chip discharging on the second cutting edge (2) side as well.

Variation of Embodiment 2

Referring to FIGS. 12 and 13, a drill (D) is equipped with a configuration wherein the first cutting edge (1) and the second cutting edge (2) are provided with a first back groove (7) and a second back groove (8) from the rearward ends of the outer peripheries of the first cutting edge (1) and the second cutting edge (2) to the first relief surface (3) and the second relief surface (4), respectively, and also provided with a first margin portion (M1) and a second margin portion (M2) of the first cutting edge (1) and the second cutting edge (2), respectively.

The drill (D) according to the present variation is similar to the drill (D) illustrated in the aforementioned FIGS. 7 and 8 in that the first back groove (7) and the second back groove (8) as well as the first margin portion (M1) and the second margin portion (M2) can be formed on the outer peripheries as appropriate depending on the drilling depth, and the portions with the first back groove (7) and the second back groove (8) are thinner than the first margin portion (M1) and the second margin portion (M2), thus only the first margin portion (M1) and the second margin portion (M2) will be in contact with the wall surface of the drilled hole, thereby reducing friction during drilling.

The first back groove (7) and second back groove (8) may be formed only on the outer periphery of the side of the first cutting edge (1) the contact area of which is large, or only on the outer periphery of the side of the first cutting edge (1) may have a double-margin shape (not shown).

Regarding the formation of the first back groove (7), since it is not necessary to form an exact cylindrical surface by grinding with a grinding wheel, which is a means for formation, it is acceptable for ridgelines indicating the boundaries of the grinding trace of the grinding wheel to appear.

In the figures explained above in Embodiment 1 and Embodiment 2, the lengths of chip-discharging grooves are shown as one circumference of the outer periphery of the drill, but it is not limited to this length and may be determined depending on the subject of surgery (drilling).

While not limited thereto, the specifications of the drill (D) according to Embodiments 1 and 2 are as follows.

The diameter of the drill is about 2 mm to 6 mm; the point angle is 40° to 90°; the relief angle is 5° to 30°; the helix angle (chip-discharging groove) is 15° to 20°; the length of the groove (chip-discharging groove) is about ¼ of the circumference (determined by the subject of surgery); and the total length of the drill is determined by the subject of surgery (100 mm or more).

Examples

The drill according to the present invention will be further explained in detail based on the following examples. However, the drill according to the present invention is not limited to the examples.

To confirm the performance of the drill according to the present invention, 1) cutting resistance test, 2) inclined surface cutting test, and 3) bending test were conducted.

A drill (Product name: "GEKKOU DRILLS FOR MEDICAL USE") from the aforementioned Japanese Unexamined Patent Application Publication No. 2018-108223 was used as a reference drill to the drill according to the present invention.

<Common Specifications>

Drill diameter: 2.4 mm

Total length: 200 mm (when used in a cutting test)
70 mm (when used in a bending test: cut)

Groove length: 8 mm (jig fixing position during the bending test)

Material: JIS, SUS316L stainless steel (1) Cutting Resistance Test (Torque, Thrust)

Workpiece: simulated bone, manufactured by SAWBONES; Material: Solid rigid polyurethane; density 50 pcf (Product No.: SAW1522-27); width 6 mm; thickness 6 mm Cutting Conditions Rotation rate: 1,000 RPM Feed speed: 120 mm/min (0.12 mm/rev)

Distance from chuck to forward end of the drill during the cutting test: 150 mm (2) Inclined Surface Cutting Test Cutting was performed on a surface inclined at 40° from the horizontal, and the displacement of the hole position after cutting was measured.

A surface inclined at 40° was formed on a test piece made of the same material as in (1), and the position of the center of the hole after drilling was measured to confirm the displacement of the position.

The reference position of the hole was X=10 and Y=7.5 (mm) from the reference point.

The position of the hole after drilling was measured based on this reference position, and a displacement amount L was calculated using the formula $L=\sqrt{(X-10)^2+(Y-7.5)^2}$.

(e.g., L=0.71 for X=10.5 and Y=8.0)

Cutting Conditions

Rotation rate: 300 RPM

Feed speed: 43.26 mm/min

The same material as in (1) was used.

(3) Bending Test (Strength and Stiffness Test)

The total length of the drill was cut to 70 mm, the drill was fixed at 8 mm from the forward end such that the chip-discharging grooves were oriented <1> upwardly (0°) or <2> laterally (90°), a load was applied at a speed of 10 mm per minute to a position 50 mm from the fixing position until the displacement of the rearward end reached 15.4 mm, and then the load applied at that point was checked.

(3) Test Results (3-1) Cutting Resistance Test

Cutting resistance and rotational torque resistance against the aforementioned simulated bone manufactured by SAWBONES were measured to compare the maximum values.

The drill according to the present invention (Example) and the drill according to the Comparative Example (Japanese Unexamined Patent Application Publication No. 2018-108223) were used to drill a through hole two times each.

The results are shown in the table below.

TABLE 1

| Test | Drilling times | Reference drill | Drill according to the present invention | Ratio (%) of the drill according to the present invention |
|---|---|---|---|---|
| Max. rotational torque resistance [N · mm] | first time | 55.4 | 33.1 | 60 |
| | second time | 50.3 | 32.4 | 64 |
| Max. thrust load resistance (Cutting resistance) [N] | first time | 9.9 | 8.5 | 86 |
| | second time | 8.2 | 7.4 | 90 |

The results of the cutting test showed the superiority of the present drill (the drill according to the Example) in terms of thrust resistance and torque resistance.

In other words, the torque resistance of the present drill (the drill according to the Example) was found to be 60% (first time) and 64% (second time) as compared with that of the reference drill (the drill according to the Comparative Example); that is, be reduced by 40% less (first time) and 36% less (second time) as compared with that of the reference drill (the drill according to the Comparative Example).

On the other hand, the thrust load resistance ratio of the present drill (drill according to the Example) was found to be 86% (first time) and 90% (second time) as compared with that of the reference drill (drill according to Comparative Example); that is, be reduced by 14% less (first time) and 10% less (second time) as compared with that of the reference drill (drill according to Comparative Example).

From the above results, it was confirmed that the present drill (drill according to the Example) has superior cutting ability equivalent to or superior to the reference drill (drill according to Comparative Example).

(3-2) Inclined Surface Cutting Test

Each drill was subjected to drilling tests five times to confirm the displacement of the drilling portion on the inclined surface.

TABLE 2

| Drill | Drilling times | Center position of drilling X | Center position of drilling Y | Displacement X | Displacement Y | Displacement amount L |
|---|---|---|---|---|---|---|
| Reference Drill | 1 | 8.94 | 7.57 | −1.06 | 0.07 | 1.062 |
| | 2 | 8.87 | 7.31 | −1.13 | −0.19 | 1.146 |
| | 3 | 9.25 | 7.45 | −0.75 | −0.05 | 0.752 |
| | 4 | 9.68 | 7.47 | −0.32 | −0.03 | 0.321 |
| | 5 | 9.53 | 7.43 | −0.47 | −0.07 | 0.475 |
| | | Average for five times | | | | 0.751 |
| Present drill | 1 | 10.34 | 7.22 | 0.34 | −0.28 | 0.440 |
| | 2 | 9.79 | 7.33 | −0.21 | −0.17 | 0.270 |
| | 3 | 10.34 | 7.32 | 0.34 | −0.18 | 0.385 |
| | 4 | 10.02 | 7.34 | 0.02 | −0.16 | 0.161 |
| | 5 | 9.92 | 7.26 | −0.08 | −0.24 | 0.253 |
| | | Average for five times | | | | 0.302 |

As shown above, the average of displacement amount was 0.302 mm for the present drill (Example) and 0.751 mm for the reference drill (Comparative Example).

Further, the maximum of displacement amount was 0.440 mm for the present drill (Example) and 1.146 mm for the reference drill (Comparative Example);

and the minimum was 0.161 mm for the present drill (Example) and 0.321 mm for the reference drill (Comparative Example), which revealed the superiority of the present drill (Example) in terms of drilling on an inclined surface. Especially, it was found that more than half of the displacements in the X direction were made to the +side (upward direction), which indicated the superiority of the present drill in terms of drilling on an inclined surface. (All the displacements of the reference drill (Comparative Example) were made to the −side (displaced downward))

(3-3) Bending Test (Strength Test)

The results are shown in the table below (Table 3).

TABLE 3

| Direction of chip-discharging groove | Drill | Max. bending load (N) | Ratio |
|---|---|---|---|
| 0° | Reference drill | 18.25 | 1 |
| | Present drill | 33.03 | 1.81 |
| 90° | Reference drill | 38.39 | 1 |
| | Present drill | 50.77 | 1.32 |

As shown in Table 3, it was confirmed that the present drill (Example) has higher strength than the reference drill. Especially, the strength in the direction that is easy to break (0°) was confirmed to be superior.

According to the above results,

1) In the cutting resistance test, the present drill (Example) has:

both higher cutting resistance in the forward direction and rotational torque resistance in the rotation direction as compared with the drill according to the Comparative Example (Japanese Unexamined Patent Application Publication No. 2018-108223), especially the rotational torque resistance was significantly higher, thus confirming that the present drill has superior cutting ability and can drill with less force.

2) In inclined surface cutting test, the present drill (Example) has:

superiority shown in drilling on inclined surfaces as compared with the drill according to the Comparative Example (Japanese Unexamined Patent Application Publication No. 2018-108223).

This can be assumed to be due to the superior stiffness of the drill itself, which makes it hard to bend and reduces the factors for the forward end of the drill to slip, and the superior cutting ability (especially torque: cutting ability in the rotation direction) of the forward end, which resulted in a smaller amount of displacement.

3) In the bending test (strength test), the present drill (Example) has:

superior strength and stiffness as compared with the drill according to the Comparative Example (Japanese Unexamined Patent Application Publication No. 2018-108223), which were clearly shown by the numerical values.

INDUSTRIAL APPLICABILITY

The drill according to the present invention is equipped with: a first and a second cutting edge formed symmetrically with respect to a rotation axis; a first relief surface and a second relief surface formed symmetrically with respect to the rotation axis on back surfaces of the first and the second cutting edge, respectively; one chip-discharging groove formed from one of the first and the second cutting edge toward an outer peripheral side; and one or more arc-shaped grooves formed from another of the first and the second cutting edge toward the outer peripheral side, and thus breakage of the drill can be prevented.

Further, since the drill according to the present invention is not thinned and the chip-discharging groove can be formed up to near the center portion of the drill, the chip-discharging groove itself can exhibit the same effect (i.e., good cutting ability) as if a thinning process is applied.

Further, since the drill according to the present invention comprises a first and a second relief surface formed symmetrically with respect to the rotation axis, the occurrence of troubles such as the center portion being out of control at the start of drilling is suppressed.

Therefore, the drill according to the present invention with superior rotational torque resistance and cutting ability is used not only for drilling holes in a workpiece such as a metal plate with a hand drill, a drill press, or the like without breaking, but also used for drilling holes directly in a surgical area during a medical surgery, especially in an orthopedic surgery. Further, besides being used as a drill for drilling holes directly in a surgical area, the drill according to the present invention is used as a fixed rotation center for drilling with a hollow drill (i.e., a through hole equivalent to a small-diameter drill in the rotation center portion) after drilling and fixing with a small-diameter drill, also known as a guide pin, a guide wire, an eyelet pin, etc., into a surgical area such as a bone or a joint in advance as a rotation center when drilling with a hollow drill.

EXPLANATIONS OF REFERENCES

1 First cutting edge
2 Second cutting edge
3 First relief surface
4 Second relief surface
**4*a*** Third relief surface
5 Chip-discharging groove
**6*a*, 6*b*, 6*c*** Arc-shaped groove
7 First back groove
8 Second back groove
D Drill
M1 First margin portion
M2 Second margin portion
θ1 Rake angle of the first cutting edge
θ2 Rake angle of the second cutting edge

What is claimed is:

1. A drill comprising:

a first and a second cutting edge formed symmetrically with respect to a rotation axis;

a first and a second relief surface formed symmetrically with respect to the rotation axis on back surfaces of the first and the second cutting edge, respectively;

one chip-discharging groove formed from one of the first and the second cutting edge toward an outer peripheral side;

one or more arc-shaped grooves formed from another of the first and the second cutting edge toward the outer peripheral side;

wherein two or more of the are shaped grooves are formed to be adjacent to each other, one of the two or more arc-shaped grooves and the first relief surface are partially adjacent to each other, and another one of the two or more arc-shaped grooves and the second relief surface are adjacent to each other; and wherein the first and the second cutting edge are provided with a first and a second back groove from the rearward ends of the outer peripheries of the first and the second cutting edge to the first and the second relief surface respectively, and also provided with a first and a second margin portion of the first and the second outing edge, respectively.

* * * * *